US006478788B1

(12) United States Patent
Aneas

(10) Patent No.: US 6,478,788 B1
(45) Date of Patent: Nov. 12, 2002

(54) DEVICE FOR CONNECTION BETWEEN A RECIPIENT AND A CONTAINER AND READY-TO-USE ASSEMBLY COMPRISING SUCH A DEVICE

(75) Inventor: Antoine Aneas, Menetrol (FR)

(73) Assignee: Biodome, Issoire (FR)

( * ) Notice: Subject to any disclaimer, the term of this patent is extended or adjusted under 35 U.S.C. 154(b) by 0 days.

(21) Appl. No.: 09/497,475

(22) Filed: Feb. 4, 2000

(30) Foreign Application Priority Data

Feb. 10, 1999 (FR) ........................................... 99 01755

(51) Int. Cl.[7] .......................... A61B 19/00; A61M 5/32

(52) U.S. Cl. ......................... 604/411; 604/86; 604/414; 604/415; 215/247

(58) Field of Search ................................ 604/403, 411, 604/414, 415, 86–89, 200, 201, 905; 215/247, 249, DIG. 3; 222/83

(56) References Cited

U.S. PATENT DOCUMENTS

| | | | | |
|---|---|---|---|---|
| 3,977,555 A | | 8/1976 | Larson | 215/247 |
| 5,879,345 A | | 3/1999 | Aneas | 604/411 |
| 6,070,623 A | * | 6/2000 | Aneas | 604/403 |
| 6,090,093 A | * | 7/2000 | Thibault et al. | 604/411 |

FOREIGN PATENT DOCUMENTS

| | | |
|---|---|---|
| WO | WO 90/03536 | 4/1990 |
| WO | WO 97/10156 | 3/1997 |
| WO | WO 98/13006 | 4/1998 |
| WO | WO 98/32411 | 7/1998 |

* cited by examiner

*Primary Examiner*—David J. Walczak
*Assistant Examiner*—Tuan Nguyen
(74) *Attorney, Agent, or Firm*—Oliff & Berridge, PLC

(57) ABSTRACT

A device for connecting between a recipient and a container, including a base, mounted on the recipient and a bush forming an inner bore, and a plunger adapted to slide in this bore, between a first position disengaged with respect to the stopper of the recipient and a second, so-called transfer position, in which a hollow needle borne by the plunger traverses the stopper. The base is provided with at least one elastic catch for retaining the plunger in the transfer position, this catch projecting, from the bush, towards the interior of the bore and being adapted to cooperate with an outer radial tab of the plunger.

13 Claims, 4 Drawing Sheets

DEVICE FOR CONNECTION BETWEEN A RECIPIENT AND A CONTAINER AND READY-TO-USE ASSEMBLY COMPRISING SUCH A DEVICE

FIELD OF THE INVENTION

The present invention relates to a device for connection between a closed recipient and a container, and to a ready-to-use assembly comprising, inter alia, a closed recipient and a connection device of the afore-mentioned type.

BACKGROUND OF THE INVENTION

In the domain of packaging medicines, it is known to store one component of a pharmaceutical preparation, such as for example its active ingredient, in a recipient closed by a relatively non-rigid material, for example made of elastomer. A liquid may be introduced info this recipient, after perforation of the stopper, in order to place the component contained in the recipient in solution or in suspension, so as to obtain a preparation, in particular a medicament or vaccine, in liquid form ready to be administered to the patients.

Documents WO-A-90/03536 and WO-A-97/10156 disclose connection devices, each comprising a base adapted to cover the neck of a recipient and extended by a flange or bush forming an inner bore, while a plunger is mounted to slide in this bore. The plunger is provided to be pushed towards a transfer position in which a hollow needle borne by the plunger passes through the stopper of the recipient. These known devices allow axial movements of the plunger when it has been displaced up to transfer position, which might lead to leakages and does not efficiently control the lost volume of the recipient, i.e. the quantity of liquid which cannot be drawn off therefrom.

Document WO-A-98/13006 discloses a device adapted, in particular, for connection between a recipient with a stopper which is adapted to be perforated and a syringe, in which teeth are distributed about the axis of the plunger and provided to be returned centrifugally or centrapetally in order to cooperate with a stop clement provided on a base. This device allows a locking of the plunger as long as the effort of displacement to which it is subjected is not too great. However, under certain conditions, the teeth might be deformed plastically, which might allow the plunger to tear in a direction of extraction.

It is a particular object of the present invention to overcame these drawbacks, by proposing an unproved connection device in which a particularly efficient locking of the plunger in transfer position is obtained

SUMMARY UP THE INVENTION

To that end, the invention relates to a device of the type mentioned above, in which the base is provided with at least one elastic catch for retaining the plunger in transfer position, this catch projecting from the bush towards the interior of the bore and being adapted to cooperate with an outer radial tab of the plunger.

Thanks to the invention, the elastic catch guarantees a efficient locking of the plunger in transfer position. Such locking is all the more efficient as a plurality of catches are advantageously provided, which may be regularly distributed about the central axis of the device.

According to a first advantageous aspect of the invention, the catch is provided, on an outer radial face, with a heel adapted to cooperate with a ring for locking the plunger in position of retention, this ring being adapted to slide about the bush. This ring gives the retaining catch a sufficient rigidity to efficiently resist an effort of displacement of the plunger from the transfer position. This ring is advantageously provided with an outer radial flange for locking in translation in a position of cooperation with the catch.

According to another advantageous aspect of the invention, the device comprises means for locking in rotation the plunger and/or the locking ring. These means advantageously comprise longitudinal ribs made on the inner face and/or the outer face of the bash and adapted to cooperate with corresponding elements in relief provided on the outer radial surface of the plunger and/or on the inner radial surface of the ring.

According to another advantageous aspect of the invention, in disengaged position with respect to the stopper, the plunger is fast with the bush by at least one breakable tongue. In addition, the base and the plunger are advantageously formed in one piece by injection of plastics material. This facilitates positioning of the plunger with respect to the base, insofar as this positioning results directly from the method of manufacture and as it is not necessary to provide an assembly step corresponding to the insertion of the plunger in the base. Moreover, the one-piece nature of the base and plunger guarantees that the plunger dues not risk sliding in the bore, particularly under the effect of vibrations or sudden accelerations during transport of the device. In this way, the tip of a needle borne by the plunger is held for certain inside the bare, with the result that it does not risk projecting beyond the base to the point of marking or perforating a stopper when the device is positioned on the recipient. With the known devices, such a risk could not be completely eliminated, including when using beads for holding the plunger.

According to another advantageous aspect of the invention, a cap for protecting the bore and the plunger is provided, on an inner face, with a member for transmission of a thrust effort for the displacement of the plunger from the first position towards the second position. In this way, the protecting cap serves as member for maneuvering the plunger.

According to another advantageous aspect of the invention, the bush comprises, near its free edge, means for blocking the container by cooperation of shapes, in particular bayonet-type locking slots adapted to cooperate with at least one tab of the container.

According to another advantageous aspect, the base comprises a cylindrical surface defining a skirt which extends around the neck of the recipient and bears hooking teeth, this skirt comprising at least one opening far access to the catch and/or to certain hooking teeth from the outside. These openings are particularly useful for efficiently moulding the catch or catches and the corresponding teeth.

The invention also relates to a ready-to-use assembly comprising a closed recipient containing a product, in particular a pharmaceutical preparation, this recipient being provided with a neck whose opening is obdurated by a stopper, and a connection device as described hereinabove, mounted on the recipient. Such an assembly enables a component of a medicine or a vaccine, in particular its active ingredient, to be kept sterile and to be prepared when necessary by mixture with a liquid, while its plunger is efficiently held in position.

BRIEF DESCRIPTION OF THE DRAWINGS

The invention will be more readily understood in reading the following description of an embodiment of a connection device in accordance with its principle, given solely by way of example, with reference to the accompanying drawings, in which.

DESCRIPTION OF PREFERRED EMBODIMENT

Figure 1:
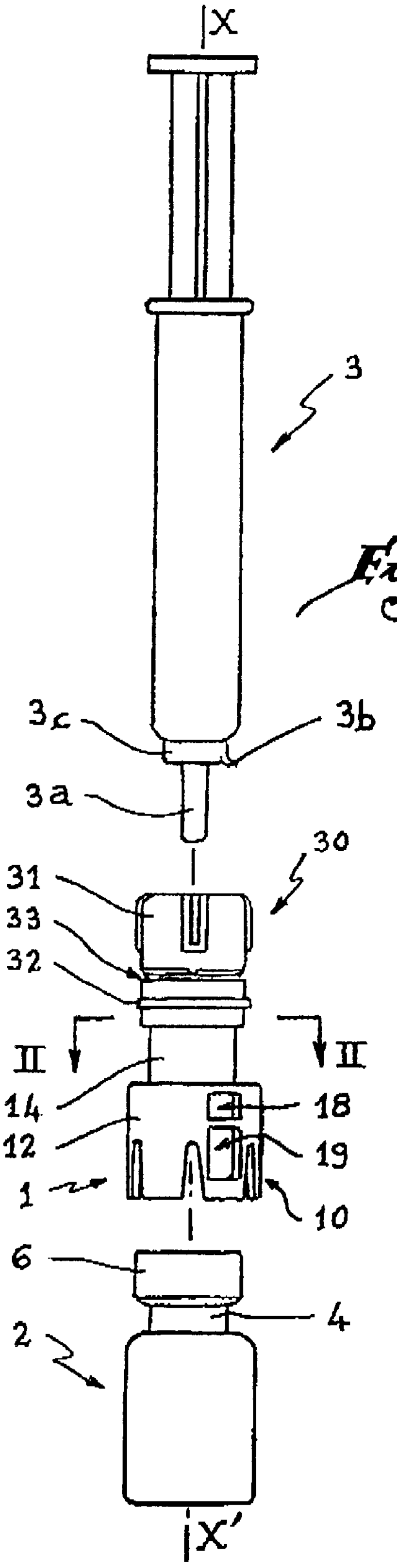
FIG. 1 is an exploded side view of a ready-to-use assembly according to the invention.

Referring now to the drawings, the device according to the invention has a dual function. On the one hand, it guarantees the tamper-proof nature of a recipient 2, for example a glass bottle containing a product (not shown) and previously closed or stopped. This product may be a powder intended to form a drinkable vaccine, or it may be question of any other type of pharmaceutical preparation, in particular any type of medicine. On the other hand, the device 1 ensures or establishes a tight connection between the interior of the recipient 2 and the interior of another container 3, such as a syringe containing a liquid intended to place the product contained in the recipient 2 in solution or in suspension. Instead of a syringe, the container 3 might be formed by a supple bag or another glass bottle.

The recipient 2 comprises a neck 4, whose opening 4*a* is tightly obdurated by a clapper 5 made of a relatively non-rigid material, for example elastomer and, in particular, rubber. The neck 4 comprises an outer annular bead 4*b* on which is crimped a capsule b which also covers a peripheral part of the stopper 5 and which is provided with a central opening 6*a* through which it is possible to perforate the stopper 5. The stopper 5 comprises a substantially cylindrical central part 5*a*, adapted for supple and tight fit inside the opening 4*a*, and a flattened outer part 5*b*, shouldered by the bead 4*a*, and covered by the capsule 6.

The device 1 is essentially formed by two parts made by injection of plastics material, for example polyethylene, polypropylene, polyamide or ABS (polyacrylonitrile/butadiene/styrene), namely a base element 10 intended to be mounted around elements 4 to 6, and a cap 30.

Figure 3:
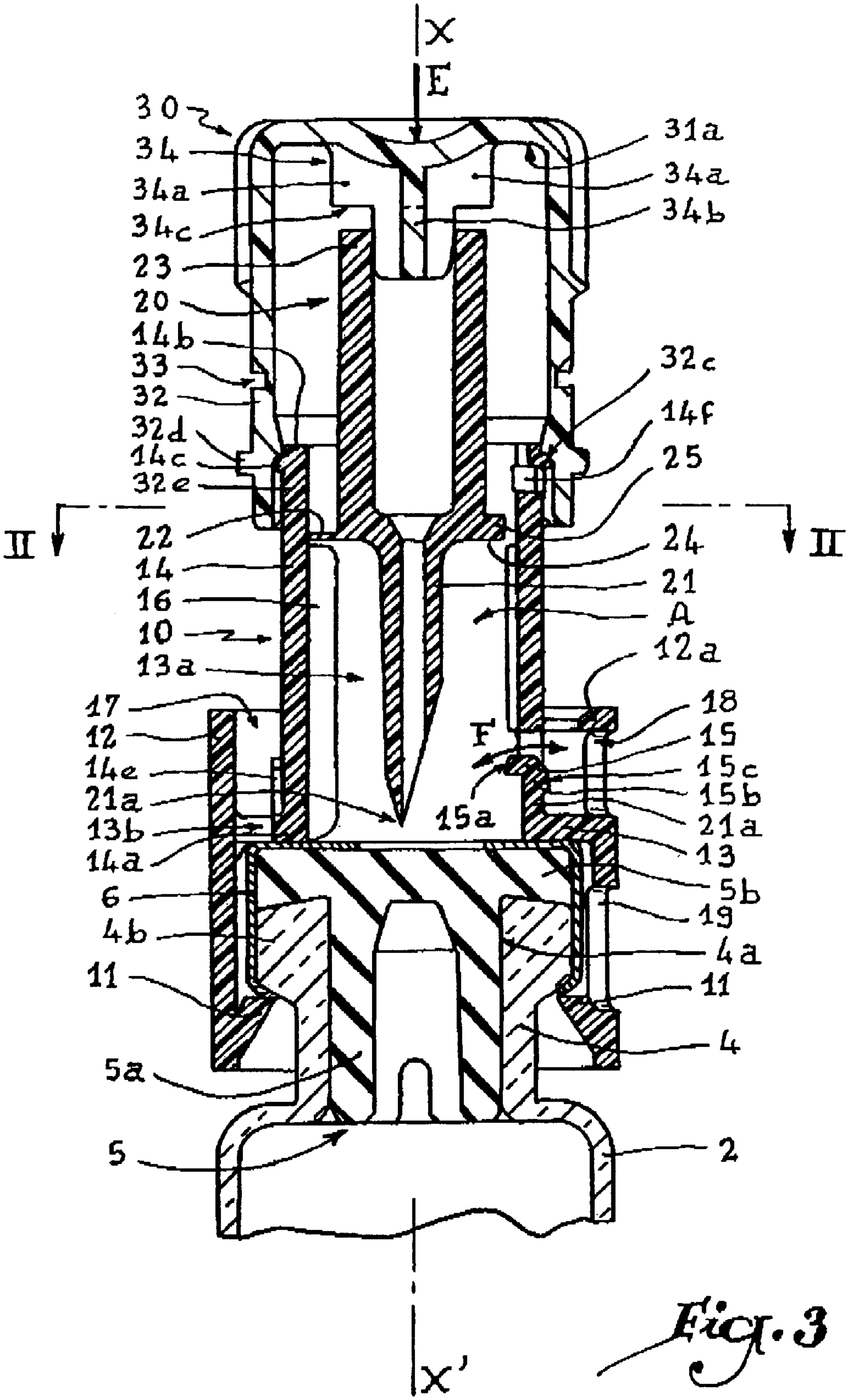
FIG. 3 is a broken section along line III—III in FIG. 2, the plane of section of FIG. 2 being indicated at II—II.

The base element 10 comprises a plurality of hooking teeth 11 provided to be arranged around the bead 4*b*, as shown in FIG. 3. These teeth are defined in the lower part of a cylindrical skirt 12 surrounding the neck 4. The element 10 comprises a wall 13 for abutment on the upper part of the capsule 6, this wall being provided with a central recess 13*a* bordered by a cylindrical bush 14, concentric to the skirt 12 and extending opposite the wail 13 with respect to said skirt.

XX' denotes the central axis of the device 1 which is, in particular, the axis of the skirt 12 and of the bush 14. The bush 14 extends up to contact with the capsule 6 and defines a bore A centred on axis XX'.

In its part 14*a* closest to the stopper 5, the bush 14 is equipped with two catches 15 and 15 'projecting radially towards the interior of the bore A. Taking into account the plastic material used for moulding element 10, these lips are supple enough to be elastically deformed, as represented by arrow F in FIG. 3.

Figure 2:
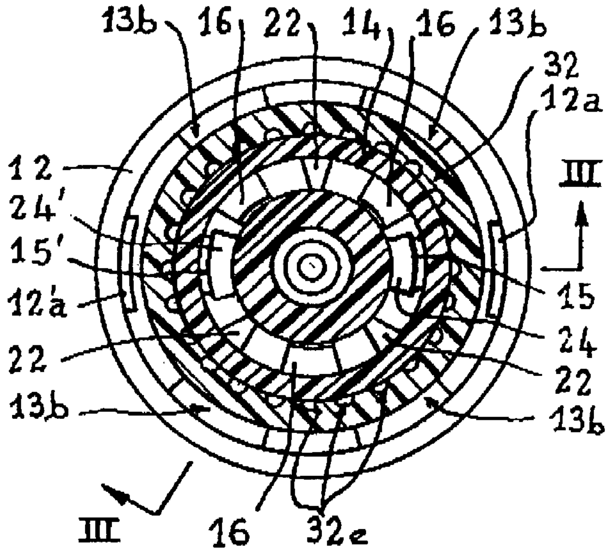
FIG. 2 is a transverse section along line II—II of FIG. 1.

As is clearly visible in FIG. 2, the catches 15 and 15' are diametrally opposite. However, other distributions, as well as a different number of retaining catches, may be envisaged.

Inside bore A is disposed a plunger 20 forming a hollow needle 21 adapted to perforate the stopper 5 in its central part. Plunger 20 is connected to the bush 14 by tongues 22 which are three in number and regularly distributed on the periphery of the plunger 20. In this way, the plunger 20 is in one-piece with the base 10 until the tongues 22 are broken.

Plunger 20 also forms a sleeve 23 for receiving the nose 3*a* of the syringe 3. The inner diameter of the sleeve 23 is chosen to be sufficiently small for only those syringes that may be introduced therein to correspond to a special manufacture intended for this use.

Plunger 20 bears two tabs 24 extending radially outwardly at the level of the transition zone 25 between the needle 21 and the sleeve 23.

On its inner radial surface, the bush 14 bears three longitudinal ribs 16 which cooperate with the sides of the tabs 24 to avoid a rotation of the plunger 20 about axis XX'.

The cap 30 is formed by a removable part 31, surrounding the free edge 14*b* of the bush 14, and by a ring 32 disposed around the bush 14, parts 31 and 32 being connected by a breakable zone 33.

Near its free edge 14*b*, the bush 14 is provided with an outer ring 14*c* provided to penetrate in an inner peripheral groove 32*c* of the ring 32. These outer ring and groove make it possible to maintain the cap 30 in position with respect to the element 10 in the storage position of FIGS. 1 to 3. The device 1 may he maintained in position on bottle 2 for several months, before use.

On its inner face 31*a*, part 31 is equipped with an extension 34 whose shape is adapted to be able to engage partially in the sleeve 23. In cross-section, this extension is in the form of a cross, as it is formed by two substantially orthogonal ribs 34*a* and 34*b* intersecting at the level of axis XX'. In the position of FIG. 3, the positioning of extension 34, and in particular its depth of penetration in sleeve 23, is determined by the cooperation of the ring 14*c* and the groove 32*c*.

When it is necessary to mix the contents of syringe 23 and of recipient 2, an effort, represented by arrow E in FIG. 3, is exerted on part 31 of the cap 30, which has the effect of bearing the shoulders 34*c* of the ribs 34*a* and 34*b* against the free edge of the sleeve 23, while driving groove 32*c* with respect to ring 14*c*. Ring 32 then moves along the bush 14 in the direction of wall 13. The effort transmitted by the extension 34 to the sleeve 23 has the effect of cutting the tongues 22 and of pushing the plunger 20 towards the central opening 6*a* of the capsule 6, with the result that the sharp tip 21*a* of the needle 21 penetrates in the bottle 2 through the stopper 5. Effort E is maintained until the ring 32 is received in an annular space 17 defined between the upper part of the skirt 12 and the lower part 14*a* of the bush 14. Such displacement of the ring 32 corresponds to a displacement of the plunger 20 such that the transition zone 25 between the needle 21 and the sleeve 23 is disposed in the immediate vicinity of the upper surface of the capsule 6.

Figure 4:
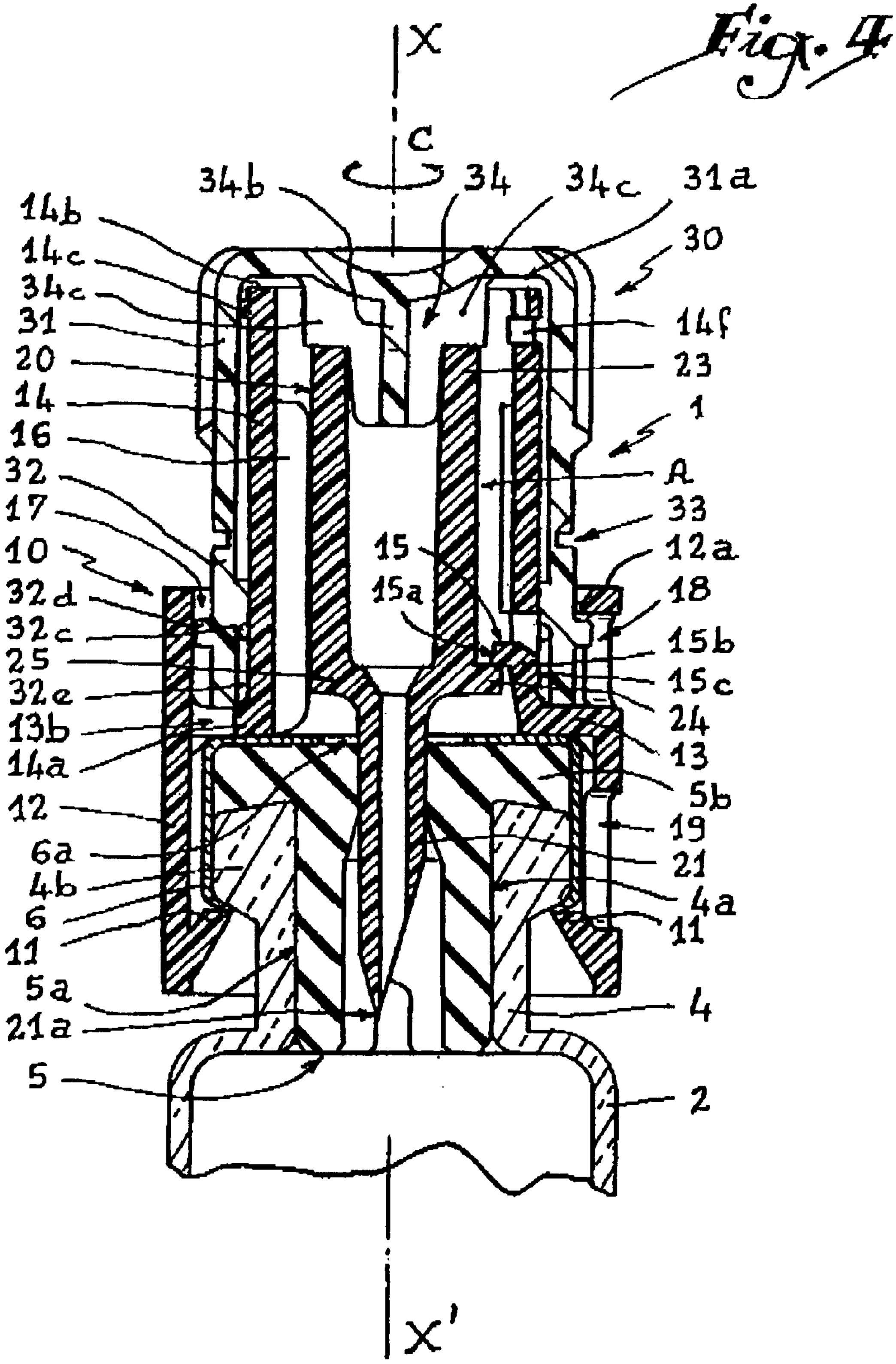
FIG. 4 is a section similar to FIG. 3 during a fast step of using the device.
Figure 5:
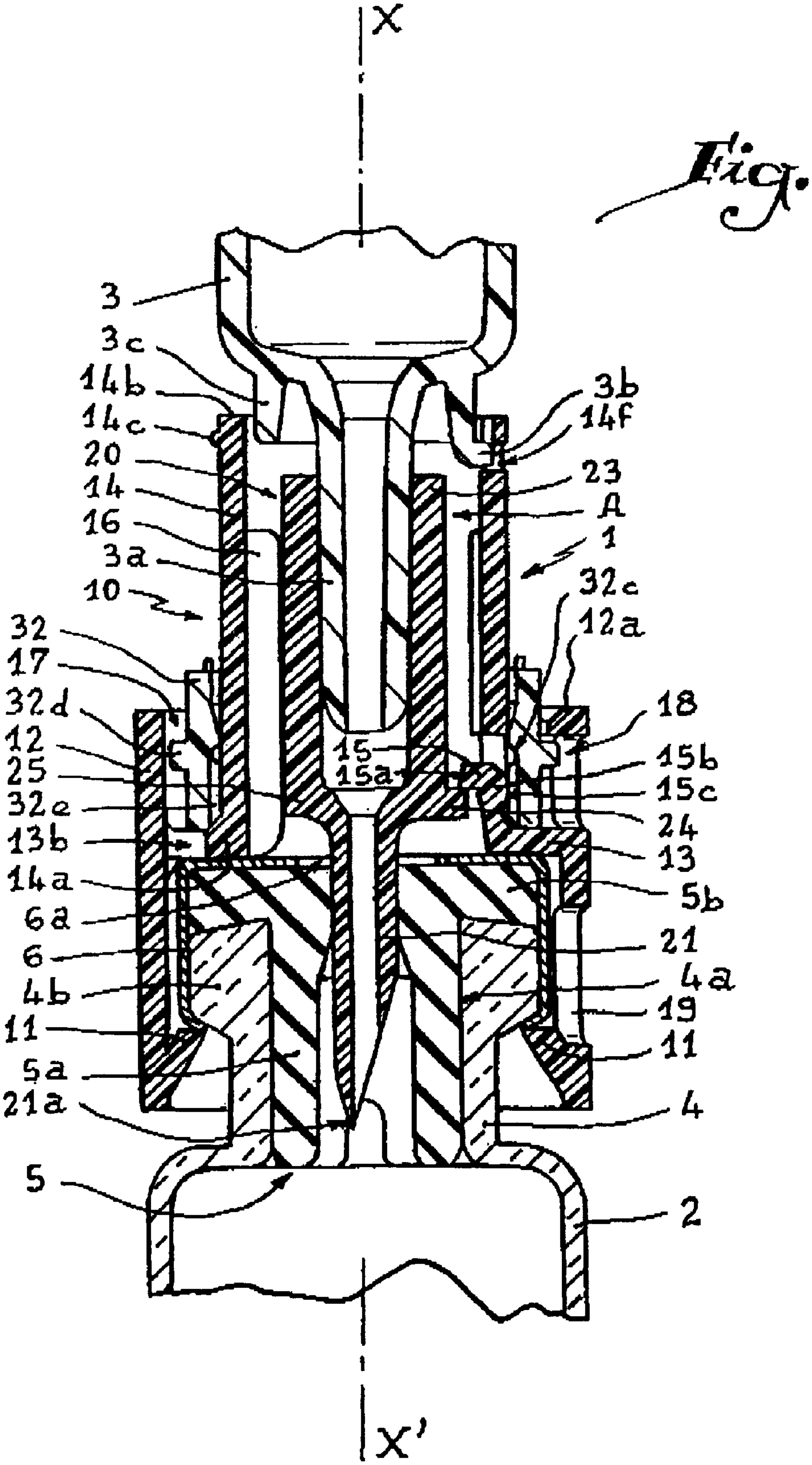
FIG. 5 is a section similar to FIG. 3 during a second step of using the device.

Such displacement of the plunger 20 has the effect of engaging the tabs 24 and 24' respectively to the rear of the catches 15 and 15', these catches being driven radially, outwardly of the bush 14, by tabs 24 and 24' during the movement of advance of the plunger 20. This is possible, as the front face 15*a* of the catch 15 visible in FIGS. 3 to 5 is inclined with respect to axis XX'. In that case, one is in the position of FIG. 4 where the ring 32 exerts on a heel 15*b*, located on a rear or outer radial surface 15*c* of the catch 15, a centripetal effort which maintains the catch 15 in an efficient locking position of the tab 24. Catch 15' which is identical, functions in the same way.

In order to guarantee a constant positioning of the ring 32 inside the volume 17, this ring is provided with an outer flange 32*d* adapted to engage beneath an upper re-entrant edge 12*a* of the skirt 12 provided on an angular sector at the level of catch 15. A similar re-entrant edge 12'*a* is provided at the level of catch 15'.

In this way, the ring 32 is firmly maintained in a position such that it prevents an elastic deformation of the catch 15 which might allow a movement of the tabs 24 in a direction moving away with respect to the stopper 5. Functioning is similar at the level of catch 15'.

At the level of its part 14*a*, the bush 14 is provided with outer ribs 14*e* provided to engage in corresponding notches 32*e* made on the inner radial surface of the ring 32.1*n* this way, in the position of FIG. 4, the ring 32 is immobilized in rotation about axis XX'. It is then possible to exert on part 31 of the cap 30 a couple 3, allowing the breakable part 33 to be broken so as to withdraw this part 31, while the ring 32 remains in position of locking of the catches 15 and 15'.

The nose 3*a* of the syringe 3 is then introduced in the sleeve 23, as shown in FIG. 5, using one or more tabs 3*b* provided at the level of a base bush 3*c* of the syringe 3 in order each to penetrate in a bayonet-type locking slot 14*f* provided near the free edge 14*h* of the bush 14. This particular construction allows an efficient locking of the syringe 3 with respect to the device 1 during the operations of transit of the liquid front the syringe towards the bottle and of recovery of the preparation in the syringe.

The bush 12 is provided at the level of catch 15, with an opening 18 which allows a mobile slide to form the rear part of the catch 15 and the re-entrant edge 12*a* of the skirt 12 during moulding. The; teeth 11 may be obtained during moulding of the element 10 by slides penetrating to the bottom of the skirt 12 through the openings 13*b* provided in the wall 13. Taking into account the geometry and location of the catch 15, this is not possible for the teeth 11 located in the same angular sector as the catch 15 and 15'. An opening l9 is provided in the skirt 12, below the opening 18, to allow the passage of a mobile slide for forming the corresponding tooth 11 during moulding of the device 1. Corresponding openings are, of course provided in the angular sector corresponding to catch 15'.

The particular structure of the catch 15 and 15' and their cooperation with the ring 32 guarantee an efficient locking of the plunger 20 in the transfer position of FIGS. 4 and 5. It will be readily understood that the number and distribution of the catches 15, 15' or equivalent depend on a choice of design within the scope of the person skilled in the art, as a function of the desired force of locking and of the rigidity of the materials used.

The invention presents the particular advantage; that it is adaptable to bottles packaged conventionally with a stopper and a crimped capsule 6, which allows it to be used after packaging of part of the medicines on a conventional chain.

The invention is applicable independently of the mode of fixing the base element 10 on the recipient 2 and, in general, it can be used in any connection device comprising a plunger mobile inside-a bore of a base mounted on a recipient.

What is claimed is:

1. A device for connection between a closed recipient and a container, said closed recipient comprising a neck whose opening is obdurated by a stopper, said connection device comprising:

a base adapted to be mounted on said recipient and comprising a bush forming an inner bore, a plunger adapted to slide in said bore, between a first position disengaged with respect to said stopper and a second position, in which a hollow needle borne by said plunger traverses said stopper, wherein said base is provided with at least one elastic catch deformable outwards of said bush, said catch projecting from said bush towards the interior of the bore for retaining the plunger in the second position and being adapted to be driven radially outwardly of said bush and substantially external of the bore by an outer radial tab of said plunger, during the movement of said plunger between the first position and the second position, and to lock said tab and said plunger in said second position.

2. The device of claim l, wherein said catch is provided, on an outer radial face, with a heel adapted to cooperate with a ring for locking said plunger in position of retention, said ring being adapted to slide around said bush.

3. The device of claim 2, wherein said ring is provided with an outer radial flange for locking in translation in a position of cooperation with said catch.

4. The device of claim 1, wherein the device comprises means for locking said plunger in rotation about a central axis of said bore.

5. The device of claim 4 wherein said means for locking in rotation comprise longitudinal ribs made on at least one of the inner face and of the outer face of said bush and adapted to cooperate with corresponding elements in relief provided on the outer radial surface of said plunger or on the inner radial surface of a ring.

6. The device of claim 1, wherein, in said disengaged position with respect to said stopper, said plunger is connected with said bush by at least one breakable tongue.

7. The device of claim 1 wherein said base and said plunger are formed in one piece by injection of plastics material.

8. The device of claim 1, wherein the device comprises a cap for protecting said bore and said plunger, said cap being provided, on an inner face, with a member for transmitting a thrust effort for the displacement of said plunger from said first position towards said second position.

9. The device of claim 1, wherein said bush comprises, near its free edge, means for locking said container with bayonet-type locking slots adapted to cooperate with at least one tab of said container.

10. The device of claim 1, wherein said base comprises a skirt which extends around said neck of said recipient and bears hooking teeth, said skirt comprising at least one opening for access to at least of one said catch or to at least one hooking teeth from the outside.

11. A ready-to-use assembly comprising a closed recipient containing a product, in particular a pharmaceutical preparation, said recipient being provided with a neck whose opening is obdurated by a stopper, and the connection device of claim 1 mounted on said recipient.

12. The device of claim 1, wherein the device comprises means for locking a ring with respect to the bush in rotation about a central axis of said bore.

13. The device of claim 12, wherein said means for locking in rotation comprise longitudinal ribs made on at least one of the inner face and outer face of said bush and adapted to cooperate with corresponding elements in relief provided on the outer radial surface of said plunger or on the inner radial surface of said ring.

* * * * *